United States Patent [19]

Rosencwaig

[11] 4,324,131

[45] Apr. 13, 1982

[54] LIQUID CHROMATOGRAPHY DETECTOR

[76] Inventor: Allan Rosencwaig, 134 Timberline Ct., Danville, Calif. 94526

[21] Appl. No.: 138,529

[22] Filed: Apr. 9, 1980

[51] Int. Cl.$^3$ .................................. G01N 15/00
[52] U.S. Cl. .................................. 73/61.1 C
[58] Field of Search ............... 73/23.1, 61.1 C, 597, 73/61.1 R; 55/67, 197

[56] References Cited

U.S. PATENT DOCUMENTS 3,892,127  7/1975  Cirulis et al. ............... 73/61.1 R
4,166,394  9/1979  Figura ......................... 73/597

Primary Examiner—Jerry W. Myracle
Attorney, Agent, or Firm—Henry P. Sartorio

[57] ABSTRACT

A method and apparatus for measuring the concentration of a solute in a solvent by measuring the change in acoustic attenuation in the solvent due to the presence of the solute. An acoustic wave generator separates a pair of identical chambers having solvent containing solute flowing through one and pure solvent through the other. Acoustic detectors are located in the chambers opposite the generator. In the amplitude differential method, acoustic waves of equal amplitude are sent into each chamber, and a differential amplitude between the attenuated waves from the two chambers is measured, from which the change in attenuation is determined. In the differential decay method, steady state resonances are excited in each chamber, and a differential amplitude between the decaying acoustic waves in each chamber is measured, from which the change in attenuation is determined.

17 Claims, 2 Drawing Figures

LIQUID CHROMATOGRAPHY DETECTOR

BACKGROUND OF THE INVENTION

The invention relates to liquid chromatography detectors and more particularly to an acoustic method for measuring the concentration of a material in a liquid chromatography effluent by measuring changes in ultrasonic attenuation.

Liquid chromatography is a separation technique in which a liquid moving phase, the effluent, is passed through a solid or a liquid stationary phase. As the mobile phase containing a mixture of compounds passes down a separation column, various compounds in the mobile phase are separated because of the difference in retention of each compound by the stationary phase. The effluent liquid thus contains a series of zones or slugs of separated compounds. Liquid chromatography is a particularly valuable technique because it is useful for large molecular weight, biochemical and/or organic mixtures and for thermally unstable and nonvolatile compounds. A liquid chromatography detector must measure the concentration of a solute in a liquid chromatography effluent. The detector must have response characteristics to measure the concentrations of the different compounds as the effluent flows through.

In the most common application of liquid chromatography separation techniques, it is desired to separate out known compounds and measure their concentrations. This procedure is critical to quality control in manufacturing processes, such as the production of drugs. It is also possible though somewhat more difficult to separate out unknown compounds for the purpose of identification of the compounds as well as obtaining a measurement of the concentration of the compound.

There are two basic detection systems presently in use for liquid chromatography. The ultraviolet detector, which measures UV absorption, is most frequently used because of its high sensitivity. However, since the ultraviolet detector relies on the presence of a strong UV absorption band within the wavelength range of the detector, it is not a universal detector and cannot be applied to all compounds of interest. Furthermore, even when the compound exhibits a suitable UV absorption band, absorption from the solvent may prevent reliable measurements at low concentrations. The refractive index detector, which measures changes in the optical refractive index, is the second most widely used detector and may be useful where a suitable UV absorption band is not present in a compound. Although the refractive index detector is a more universal sensor, its sensitivity is quite low since the optical refractive index differs by less than a factor of two for almost all liquids of interest.

Other detectors are used in more specialized and limited applications. The moving wire or transport detector produces a solute residue which is pyrolyzed. Other detectors are based on fluorescence, scintillation, heat of adsorption, infrared absorbance, electrical conductivity, capacitance, and polarography.

There is a need for a detector that is more universal than the ultraviolet detector and at the same time more sensitive than the refractive index detector. A detector is required which measures a universal physical parameter of liquids that has a wide range of values so that all liquids can be measured with the same apparatus with a sensitivity as good or better than that of the ultraviolet detector. However, unlike the situation in gases, there are few readily measurable parameters of liquids that possess a wide range of values. Most liquids have roughly similar densities, thermal properties, and refractive indices, making these parameters unsuitable for high-sensitivity detection schemes.

Accordingly, it is an object of the invention to provide a universal liquid chromatography detector with high sensitivity.

It is also an object of the invention to provide a method and apparatus for liquid chromatography detection which measures a universal physical parameter of liquids that has a wide range of values.

It is a further object of the invention to provide a universal method and apparatus to measure the concentration of a solute in a solvent.

It is another object of the invention to provide a method and apparatus for measuring ultrasonic attenuation in liquids with high sensitivity.

SUMMARY OF THE INVENTION

The invention is a method and apparatus for measuring the concentration of a compound in a solvent by measuring the change in ultrasonic attenuation in a liquid chromatography effluent due to the presence of the compound. The concentration is determined from a previously measured relation of attenuation to concentration for a known compound. Alternatively the concentration can be determined by performing calibration measurements with solutions of known concentration for compounds that are unknown or not previously measured.

The apparatus comprises a pair of identical chambers having solvent containing solute flowing through one and pure solvent through the other. An acoustic wave generator separates the two chambers and acoustic detectors are located in the chambers opposite the generator.

The invention has two preferred embodiments, the amplitude differential method and the resonance decay method. In the amplitude differential method, acoustic waves of equal amplitude are sent into each chamber, and a differential amplitude between the chambers is measured, from which the change in attenuation is determined. In the differential decay method, steady state resonances are excited in each chamber, and a differential decay rate is measured, from which the change in attenuation is determined.

DETAILED DESCRIPTION OF THE PREFERRED EMBODIMENTS

The invention is a method and apparatus for the acoustic detection of the concentration of a compound in a liquid chromatography effluent by measuring the change in ultrasonic attenuation in the effluent due to the presence of the compound. The ultrasonic attenuation coefficient is one parameter of liquids which has a wide range of values and thus is suitable for a universal high sensitivity detector.

The ultrasonic attenuation or absorption coefficient A is defined for a planar traveling ultrasonic wave as $$u = u_o e^{-Ax}$$

where $u_o$ is the acoustic pressure of the wave at point $x = 0$ and u is the pressure at point x.

For almost all liquids at room temperature and pressure, A varies as $f^2$ where f is the frequency in Hz. Thus the normalized attenuation or absorption coefficient $N = A/f^2$ is a unique parameter for a liquid at any given pressure and temperature. The normalized attenuation or absorption coefficient, N, varies from $1-2 \times 10^{-16}$ sec$^2$/cm for liquids such as water and some alcohols, to as high as $6 \times 10^{-14}$ sec$^2$/cm for liquids like $CS_2$ and benzene. Thus N can change by more than a factor of 500, as compared with changes of less than a factor of 2 for the refractive index. Ultrasonic properties of liquids have been of interest for many years, and the attenuation coefficient has been measured for many liquids, mixtures and solutions, including aqueous solutions of electrolytes. These measurements, however, have generally not been performed with high sensitivity or at very low concentrations.

The ultrasonic attenuation in a liquid chromatography effluent can be measured by either of two embodiments of the invention, the amplitude differential method and the resonance decay method. For illustrative purposes in describing the invention, the solvent chosen is water, or at least mostly water, with a normalized N of $2 \times 10^{-16}$ sec$^2$/cm.

Figure 1:
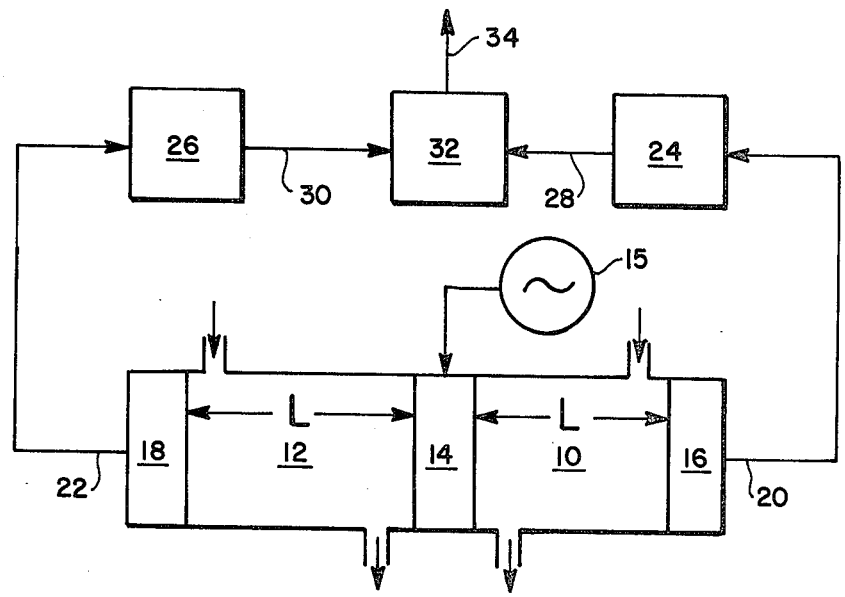
FIG. 1 is a schematic of an amplitude differential detector.

An acoustic detector for measuring the ultrasonic attenuation coefficient according to the amplitude differential method is shown in FIG. 1. The detector comprises two identical but separate chambers 10 and 12. Each chamber is preferably cylindrical from 0.1 to 1 cm in length (L) and 0.05 to 0.2 cm in diameter. The effluent (solvent plus solute) flows through chamber 10, and the carrier (solvent only) through chamber 12. The small volume allows each discrete effluent zone of differing separated material to be measured, thereby providing high chromatographic resolution. A piezoelectric driver 14 actuated by electrical generator 15 separates the two chambers 10 and 12. When activated by generator 15, the driver 14 sends acoustic waves of equal amplitude into both chambers 10 and 12 at a frequency of about 30 MHz. This frequency will result in an attenuation factor of about 0.1 for water for $L = 0.5$ cm. The chamber size is selected to provide chromatographic resolution, but is otherwise variable. For a particular L, the frequency is selected to produce an acoustic attenuation of about 10%, thereby providing measureability and linearity. The acoustic signals in the two chambers 10 and 12 are detected by the piezoelectric detectors 16 and 18, respectively, located at the ends of the chambers opposite the driver 14, producing signals 20 and 22, respectively. The signals 20 and 22 are then input into and processsed by differential tuned amplifiers 24 and 26, respectively. The amplifiers are tuned to the operating frequency. Alternatively, the signals can be prefiltered. The outputs 28 and 30 of amplifiers 24 and 26, respectively, are input into AC bridge circuit 32 which produces a difference signal 34. Other electronic circuits to measure the difference signal between the two chambers can alternatively be used. With modern electronics, a difference in the signal amplitude Q between the two chambers of $1:10^6$ can be readily detected.

The signals from the two chambers are initially balanced by the bridge circuit when only the carrier liquid or solvent (water) is flowing in both. Then any differential signal occurring when the effluent is introduced is due to a change in the ultrasonic attenuation coefficient caused by the presence of the solute. The differential signal is given by $$Q_s - Q_e = Q_o[e^{-A_s L} - e^{-A_e L}]$$

where the subscripts s and e refer to the solvent (carrier) and effluent, respectively, and $Q_o$ is the signal that would be obtained with no ultrasonic attenuation. The attenuation coefficients for the effluent and solvent are related by $$A_e = A_s + \Delta A(c)$$

where $\Delta A(c)$ is the change in the solvent's attenuation coefficient due to the presence of another compound with concentration c. Since $\Delta A(c)$ is small if c is small, the differential signal can be approximated by $$Q_s - Q_e \simeq Q_o e^{-A_s L}[\Delta A(c)L]$$

The ratio of signals 34 and 30 is thus given by $$(Q_s - Q_e)/Q_s = L \Delta A(c)$$

For a known compound of interest, if $\Delta A$ is known as a function of c, then c can be determined from the measured $\Delta A(c)$. The invention is useful for determining the concentrations of identified compounds in a solvent where the relationship between the change in attenuation and the concentration is known. If the compound is unknown or the attenuation has not been previously measured, then the invention can be used to obtain the concentration by preparing solutions of known concentrations of the compound and then using these solutions to calibrate the detector.

As an example, the sensitivity of this technique is evaluated for aqueous solutions of electrolytes. At 0.1 mole/l (c ~ 1% concentration), most electrolytes produce a change in the normalized attenuation coefficient of water in the range $10^{-17} - 10^{-15}$ sec$^2$/cm; assume a typical value of $10^{-16}$ sec$^2$/cm for a concentration $c \sim 10^{-2}$. If our detectable limit for $(Q_s - Q_e)/Q_s$ is $10^{-6}$, then for $L = 0.5$ cm, the detectable limit of $\Delta A(c)$ is $2 \times 10^{-6}$ cm$^{-1}$, or a $\Delta N(c) = \Delta A(c)/f^2 = 2 \times 10^{-21}$ sec$^2$/cm for a frequency of 30 MHz. Since a concentration of $c \sim 10^{-2}$ produces $\Delta N(c) \sim 10^{-16}$ sec$^2$/cm, then a concentration of $c \sim 10^{-7}$ will produce a $\Delta N(c) \sim 10^{-21}$ sec$^2$/cm. Thus for most electrolytes, detectable limits with the amplitude differential technique range from concentrations of $10^{-6}$ for those electrolytes that produce only small changes in N, to concentrations as low as $10^{-8}$ for some of the other electrolytes.

Figure 2:
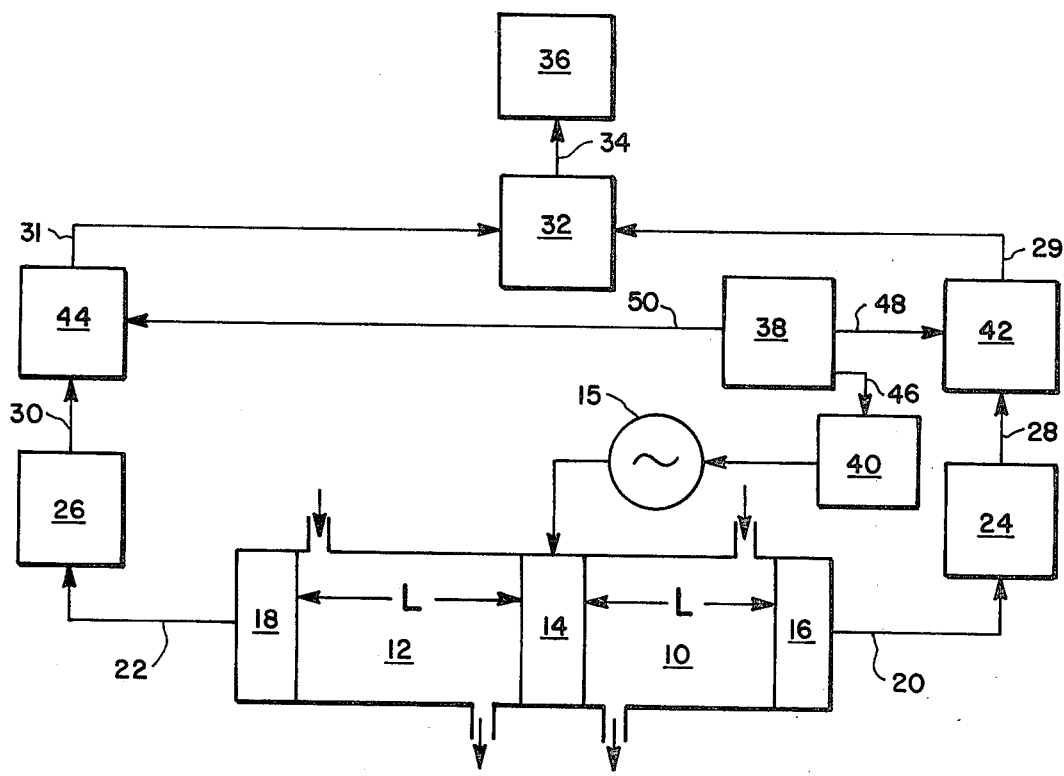
FIG. 2 is a schematic of a resonance decay detector.

The apparatus used for the resonance decay embodiment, shown in FIG. 2, is similar to that utilized for the differential amplitude embodiment. The major differences are that the lengths of the chambers, L, will be set to be at a longitudinal resonance frequency, lower frequencies (1-5 MHz) are used to enable resonances with a resonance quality q of 100 or more to be achieved, and different signal processing is required. The detector comprises two identical but separate chambers 10 and 12 through which the effluent and carrier, respectively, flow. The chambers are separated by piezoelectric driver 14. In the resonance decay technique, longitudinal resonances are excited in both chambers 10 and 12 with the ultrasonic driver 14, and then after steady-state conditions have been achieved, the driver 14 is turned off and the decay rates for the two chambers 10 and 12 are measured in a differential manner. The measurement of decay amplitudes to measure acoustic attenuation is described in R. W. Leonard, J. Acoust. Soc. Am., 18, 252 (1946) and G. Kurtze and K. Tamm, Acustica, 3, 33 (1953), which are herein incorporated by reference. The techniques described in these references are not as sensitive as the present invention since they do not use a differential cell configuration.

With effluent and carrier flowing through the chambers 10 and 12, respectively, driver 14 is actuated by generator 15 to excite longitudinal resonances in both chambers. The length of the chambers is selected to produce resonances in the range 1–5 MHz. The acoustic signals in chambers 10 and 12 are detected by piezoelectric detectors 16 and 18, respectively, located in the chambers 10 and 12 opposite driver 14, which produce signals 20 and 22, respectively. The signals 20 and 22 are respectively input into and processed by differential tuned amplifiers 24 and 26, tuned to the operating frequency, whose outputs 28 and 30, respectively are gated by gates 42 and 44, respectively, producing gated signals 29 and 31, respectively. The signals 29 and 31 are input into AC bridge circuit 32 which produces a difference signal 34 which is input into microprocessor 36.

Driver 14 is actuated by generator 15 to produce resonant acoustic waves in chambers 10 and 12. When steady state conditions are reached, driver 14 is turned off and the differential decaying amplitude of the signals in the two chambers is measured. The timing is controlled by timer 38 which sends a signal 46 to gate 40 which gates the generator 15 which actuates driver 14. The timer 38 also sends signals 48 and 50 to the gates 42 and 44, respectively, which gate the signals 28 and 30, respectively. The timing sequence for gates 42 and 44 is different from the timing sequence for gate 40. The driver 14 is turned on until steady state resonance is reached while the gates 42 and 44 are off and no signals are being processed during this time. When steady state is reached, the driver 14 is turned off and the gates 42 and 44 are turned on so that AC bridge circuit 32 can measure the differential amplitude signal. As the acoustic signal amplitudes in both chambers decay, the signal to noise ratio decreases so that at some point the measurement must be turned off and it is at this point that the gates 42 and 44 are shut off and signal processing ceases. The driver 14 is then turned on again to excite a new resonance wave in the chambers to begin another cycle of the measurement process. Because of the cyclical operation of the circuit, the signal processing requires microprocessor 36 or some other equivalent processing of the differential signal 34 over a number of cycles.

The decaying amplitude recorded by each detecting transducer 16 and 18 may be written as a function of time t as $$Q(t) = Q_o e^{-(k+Av)t}$$

where v is the sound velocity, and k is a constant which depends on other losses in the system such as those from the container, transducers and viscous effects at the container surfaces (k is assumed to be the same for both chanbers). The differential decaying amplitude between the two chambers will be given by $$Q_s - Q_e = Q_o e^{-kt} [e^{-(Av)st} - e^{-(Av)et}]$$

Using the relation $$(Av)_e = (Av)_s + \Delta(Av)$$

the relative signal difference, or the ratio of signals 34 to 31, is approximated by $$(Q_s - Q_e)/Q_s \approx \Delta(Av)t$$

In general both the attenuation coefficient and the sound velocity v will change with concentration of compound in the effluent. However, the change in velocity will be much smaller than the change in attenuation. The change in decay rate Av is given by $$\Delta(Av) = v\Delta A + A\Delta v = Av(\Delta A/A + \Delta v/v)$$

For 0.1 mol/l ($c \sim 10^{-2}$), $\Delta A/A \sim 0.5$, while $\Delta v/v \sim 10^{-3}$. So the approximation $$\Delta(Av) \approx v\Delta A$$

yields the result $$(Q_s - Q_e)/Q_s \approx vt\Delta A$$

For an unattenuated resonance of $q \sim 100$, then times $t \sim 3$ msec can be used to measure decay rates at $f \sim 3$ MHz. Then, since $v = 1.5 \times 10^5$ cm/sec for water, $$(Q_s - Q_e)/Q_s \approx 500\Delta A$$

Since the difference signal $(Q_s - Q_e)/Q_s$ can be detected in the $10^{-5}$–$10^{-6}$ range, $\Delta A$ is detectable in the $10^{-8}$–$10^{-9}$ cm$^{-1}$ range, so that concentration limits in the $10^{-7}$–$10^{-8}$ range are detectable with the resonance-decay method. Higher sensitivities might be possible by working at higher frequencies.

Although these sensitivities have been evaluated for aqueous electrolyte solutions, any compound is detectable and the calculated sensitivities will apply for almost all compounds including sugars and other substances which are difficult to detect using either the UV or refractive index detectors.

This invention is primarily a method and apparatus for a high sensitivity liquid chromatography detector. It is also clear that this invention can be used as a high sensitivity instrument for measuring the attenuation of ultrasonic waves in liquids.

Changes and modifications in the specifically described embodiments can be carried out without departing from the scope of the invention which is intended to be limited only by the scope of the appended claims.

What is claimed is:

1. A method for measuring the concentration of a solute in a solvent, comprising:
    flowing solvent containing the solute through a first chamber and flowing pure solvent through an identical second chamber;
    sending acoustic waves of equal amplitude into the two chambers;
    detecting the amplitudes of attenuated acoustic signals from each of the two chambers producing detector signals;
    measuring a difference signal between the detector signals from the two chambers;
    determining the change in acoustic attenuation of the solvent due to the presence of the solute from the measured difference signal; and determining the concentration of the solute from a predetermined relationship of the change in acoustic attenuation as a function of concentration for the solute.

2. The method of claim 1 wherein the lengths of the chambers and the frequency of the ultrasonic waves are selected to produce an ultrasonic attenuation of about 10%.

3. A method for measuring the concentration of a solute in a solvent, comprising:
flowing solvent containing the solute through a first chamber and flowing pure solvent through an identical second chamber;
exciting resonant acoustic waves of equal amplitude in the two chambers, ceasing the excitation when steady state is reached;
detecting the amplitude of decaying acoustic waves from the two chambers producing detector signals;
measuring a difference signal between the detector signals from the two chambers;
determining the change in acoustic attenuation of the solvent due to the presence of the solute from the measured difference signals; and
determining the concentration of the solute from a predetermined relationship of the change in acoustic attenuation as a function of concentration for the solute.

4. The method of claim 3 wherein the length of the chambers is selected so as to produce resonance at a frequency in the range 1–5 MHz.

5. An acoustic detector for measuring the concentration of a solute in a solvent, comprising:
a pair of identical chambers having solvent-containing solute flowing through one and pure solvent flowing through the other;
an acoustic wave generator separating the two chambers to send acoustic waves of equal amplitude into the two chambers;
detector means located in the two chambers opposite the acoustic wave generator to detect the amplitude of acoustic waves in the chambers and produce detector signals; and
processing means to process the detector signals from the two chambers and produce a difference signal between the detector signals from the two chambers.

6. The detector of claim 5 wherein the acoustic wave generator is driven continuously and the detector means detect the amplitudes of attenuated acoustic waves transmitted through the two chambers.

7. The detector of claim 6 wherein the lengths of the chambers and the frequency of the ultrasonic waves are selected to produce an ultrasonic attenuation of about 10%.

8. The detector of claim 6 wherein the processing means include a pair of differential tuned amplifiers to process the detector signals from the two chambers, respectively, and an AC bridge circuit to measure the difference signal.

9. The detector of claim 5 wherein the lengths of the chambers are selected so that the acoustic wave generator excites longitudinal resonant acoustic waves in the chambers.

10. The detector of claim 9 wherein the lengths of the chambers are selected so that resonance occurs at a frequency in the range 1–5 MHz.

11. The detector of claim 9 further including first gating means connected to the acoustic wave generator to shut off the generator when the resonant acoustic waves produced in the chambers reach steady state.

12. The detector of claim 11 wherein the processing means including second gating means to gate the detector signals from the two chambers, the second gating means being turned on when the acoustic wave generator is shut off by the first gating means.

13. The detector of claim 12 further including a timer to produce a first timing sequence to control the first gating means and a second timing sequence to control the second gating means, producing a series of operating cycles.

14. The detector of claim 13 further including a microprocessor to process the difference signal between the detector signals from the two chambers over the series of operating cycles.

15. A method for measuring small changes in the attenuation of acoustic waves in liquids, comprising:
flowing a first liquid with a known acoustic attenuation through a first chamber;
flowing a second liquid having different physical and chemical properties through an identical second chamber;
sending acoustic waves of equal amplitude from a generator into each chamber;
detecting the amplitudes of acoustic signals from each of the two chambers with detectors, producing detector signals;
measuring a difference signal between the detector signals from the two chambers; and
determining the acoustic attenuation of the liquid in the second chamber from the difference signal.

16. The method of claim 15 wherein the generator is driven continuously and the detectors detect the amplitudes of attenuated acoustic waves transmitted through the two chambers.

17. The method of claim 15 wherein the generator is driven until steady state resonant acoustic waves are produced in the two chambers and then shut off, and the detectors detect the amplitude of decaying acoustic waves in the two chambers.

* * * * *